(12) United States Patent
Wickramasinghe (10) Patent No.: US 8,904,561 B2
(45) Date of Patent: Dec. 2, 2014

(54) MECHANICAL DETECTION OF RAMAN RESONANCE

(76) Inventor: H. Kumar Wickramasinghe, Irvine, CA (US)

( * ) Notice: Subject to any disclaimer, the term of this patent is extended or adjusted under 35 U.S.C. 154(b) by 0 days.

(21) Appl. No.: 14/129,291

(22) PCT Filed: Jul. 2, 2012

(86) PCT No.: PCT/US2012/045328
§ 371 (c)(1),
(2), (4) Date: Apr. 29, 2014

(87) PCT Pub. No.: WO2013/003864
PCT Pub. Date: Jan. 3, 2013

(65) Prior Publication Data
US 2014/0310839 A1    Oct. 16, 2014

Related U.S. Application Data

(60) Provisional application No. 61/503,457, filed on Jun. 30, 2011, provisional application No. 61/508,965, filed on Jul. 18, 2011.

(51) Int. Cl.
*G01N 21/65* (2006.01)
*G01N 13/16* (2006.01)
*G01Q 60/38* (2010.01)
*G01Q 60/18* (2010.01)
*G01B 5/28* (2006.01)

(52) U.S. Cl.
CPC ............... *G01Q 60/38* (2013.01); *G01N 21/65* (2013.01)
USPC .......... 850/6; 850/30; 850/33; 850/40; 850/24

(58) Field of Classification Search
CPC ....... G01Q 60/22; G01Q 20/02; G01Q 30/02; G01N 21/65; Y10S 997/868
USPC .......................... 850/6, 24, 30, 33, 40; 73/105
See application file for complete search history.

(56) References Cited

U.S. PATENT DOCUMENTS 7,498,564 B2 * 3/2009 Miles et al. .................... 250/234
8,051,493 B2 * 11/2011 Ulcinas et al. .................. 850/33
8,739,311 B2 * 5/2014 Wickramasinghe et al. ... 850/40

\* cited by examiner

*Primary Examiner* — Nikita Wells (57) ABSTRACT

An atomic force microscope based apparatus and method for detecting Raman effect on a sample of interest utilizes first and second electromagnetic sources to emit first electromagnetic radiation of frequency Vi and second electromagnetic radiation of frequency V2 onto a probe tip, which is coupled to a structure that can oscillate the probe tip. The frequency Vi and the frequency v2 are selected to induce Raman effect on a sample engaged by the probe tip that results in Raman force interactions between the probe tip and the sample. Oscillations of the probe tip due to the Raman force interactions are then measured.

10 Claims, 5 Drawing Sheets

MECHANICAL DETECTION OF RAMAN RESONANCE

CROSS REFERENCE TO RELATED APPLICATION

This application is entitled to the benefit of U.S. Provisional Patent Application Ser. No. 61/503,457, filed on Jun. 30, 2011, and U.S. Provisional Patent Application Ser. No. 61/508,965, filed on Jul. 18, 201117, which are both incorporated herein by reference.

GOVERNMENT SUPPORT

This invention was made with Government support under Grant Nos. HG-04431 and HG-04549 awarded by the National Institute of Health. The Government has certain rights in this invention.

FIELD OF THE INVENTION

The invention relates generally to microscopy. More particularly, this invention relates to the use of atomic force microscopy (AFM) for nanometer scale detection of Raman effect.

BACKGROUND

Raman effect is one of the most widely used phenomena in chemical spectroscopy. Over the past 80 years, this effect has been measured by irradiating a sample with intense monochromatic light and detecting the minute amount (one part in $10^9$) of frequency shifted scattered light. A typical Raman setup utilizes a high rejection, low insertion loss, long pass filter to reject the incident pump light. This is followed by a sensitive detector coupled to a high resolution spectrometer to record the molecular vibrational spectrum. By scanning the light beam or the sample while the Raman effect is being measured, a two-dimensional (2D) map of Raman signal can be created. However, since the effect is measured with light, the spatial resolution of Raman-based microscopy is limited by the wavelength of the light being used.

In order to enhance the spatial resolution of Raman microscopy, Raman measurement can be combined with atomic force microscope to yield a technique known as tip-enhanced Raman spectroscopy (TERS). In TERS, a metallic atomic force microscopy (AFM) tip is used to generate an enhanced near-field light, which scatters off a sample in the immediate vicinity of the tip. The scattered light is then analyzed by using far-field optics to measure the Raman effect originating from within the scattering volume. With TERS, Raman effect originating from a single molecule and spatial resolution on the order of 10 nm have been reported. However, the quality of data acquired by TERS depends very sensitively on the tip shape, in a manner that is not well controlled. In addition, the far-field background signal is much greater and interferes with the minute signal from the near-field scattering. As a result, TERS is far from being widely adopted despite its potential usefulness.

SUMMARY

An atomic force microscope based apparatus and method for detecting Raman effect on a sample of interest utilizes first and second electromagnetic sources to emit first electromagnetic radiation of frequency $v_1$ and second electromagnetic radiation of frequency $v_2$ onto a probe tip, which is coupled to a structure that can oscillate the probe tip. The frequency $v_1$ and the frequency $v_2$ are selected to induce Raman effect on a sample engaged by the probe tip that results in Raman force interactions between the probe tip and the sample. Oscillations of the probe tip due to the Raman force interactions are then measured.

An atomic force microscope based apparatus in accordance with an embodiment of the invention comprises a probe tip for engaging a sample of interest, first and second electromagnetic sources and a sensor. The probe tip is coupled to a structure that can oscillate the probe tip. The first electromagnetic source is configured to emit first electromagnetic radiation at frequency $v_1$ onto the probe tip and the second electromagnetic source is configured to emit second electromagnetic radiation at frequency $v_2$ onto the probe tip. The frequency $v_1$ and the frequency $v_2$ are selected to induce Raman effect on the sample that results in Raman force interactions between the probe tip and the sample. The sensor is configured to measure oscillations of the probe tip due to the Raman force interactions between the probe tip and the sample.

Other aspects and advantages of the present invention will become apparent from the following detailed description, taken in conjunction with the accompanying drawings, illustrated by way of example of the principles of the invention.

BRIEF DESCRIPTION OF THE DRAWINGS

FIG. 3(a) is a topography image of Coomassie blue dye molecules on glass with $(v_1-v_2)$ tuned to the 1625 $cm^{-1}$ molecular resonance. FIG. 3(b) is a simultaneously recorded stimulated Raman force gradient image corresponding to the topography image shown in FIG. 3(a). FIG. 3(c) is a topography image of Coomassie blue dye molecules on glass with $(v_1-v_2)$ tuned off the 1625 $cm^{-1}$ molecular resonance. FIG. 3(d) is a simultaneously recorded Raman image corresponding to the topography image shown in FIG. 3(c) showing no image contrast.

DETAILED DESCRIPTION

It will be readily understood that the components of the embodiments as generally described herein and illustrated in the appended figures could be arranged and designed in a wide variety of different configurations. Thus, the following more detailed description of various embodiments, as represented in the figures, is not intended to limit the scope of the present disclosure, but is merely representative of various embodiments. While the various aspects of the embodiments are presented in drawings, the drawings are not necessarily drawn to scale unless specifically indicated.

The present invention may be embodied in other specific forms without departing from its spirit or essential characteristics. The described embodiments are to be considered in all respects only as illustrative and not restrictive. The scope of the invention is, therefore, indicated by the appended claims rather than by this detailed description. All changes which come within the meaning and range of equivalency of the claims are to be embraced within their scope.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussions of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize, in light of the description herein, that the invention can be practiced without one or more of the specific features or advantages of a particular embodiment. In other instances, additional features and advantages may be recognized in certain embodiments that may not be present in all embodiments of the invention.

Reference throughout this specification to "one embodiment," "an embodiment," or similar language means that a particular feature, structure, or characteristic described in connection with the indicated embodiment is included in at least one embodiment of the present invention. Thus, the phrases "in one embodiment," "in an embodiment," and similar language throughout this specification may, but do not necessarily, all refer to the same embodiment.

Figure 1:
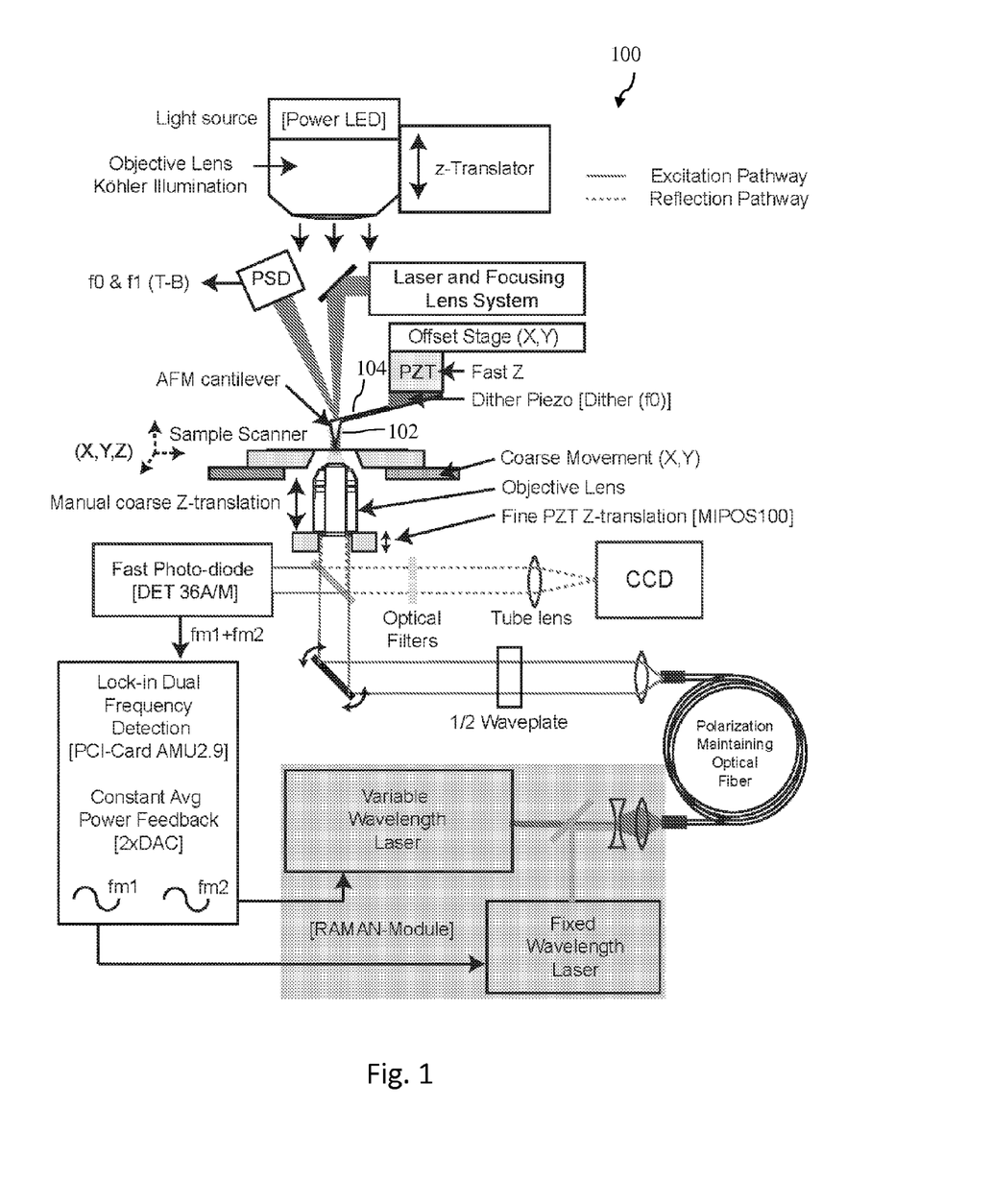
FIG. 1 is a diagram of a Raman force microscope in accordance with an embodiment of the invention.
Figure 2:
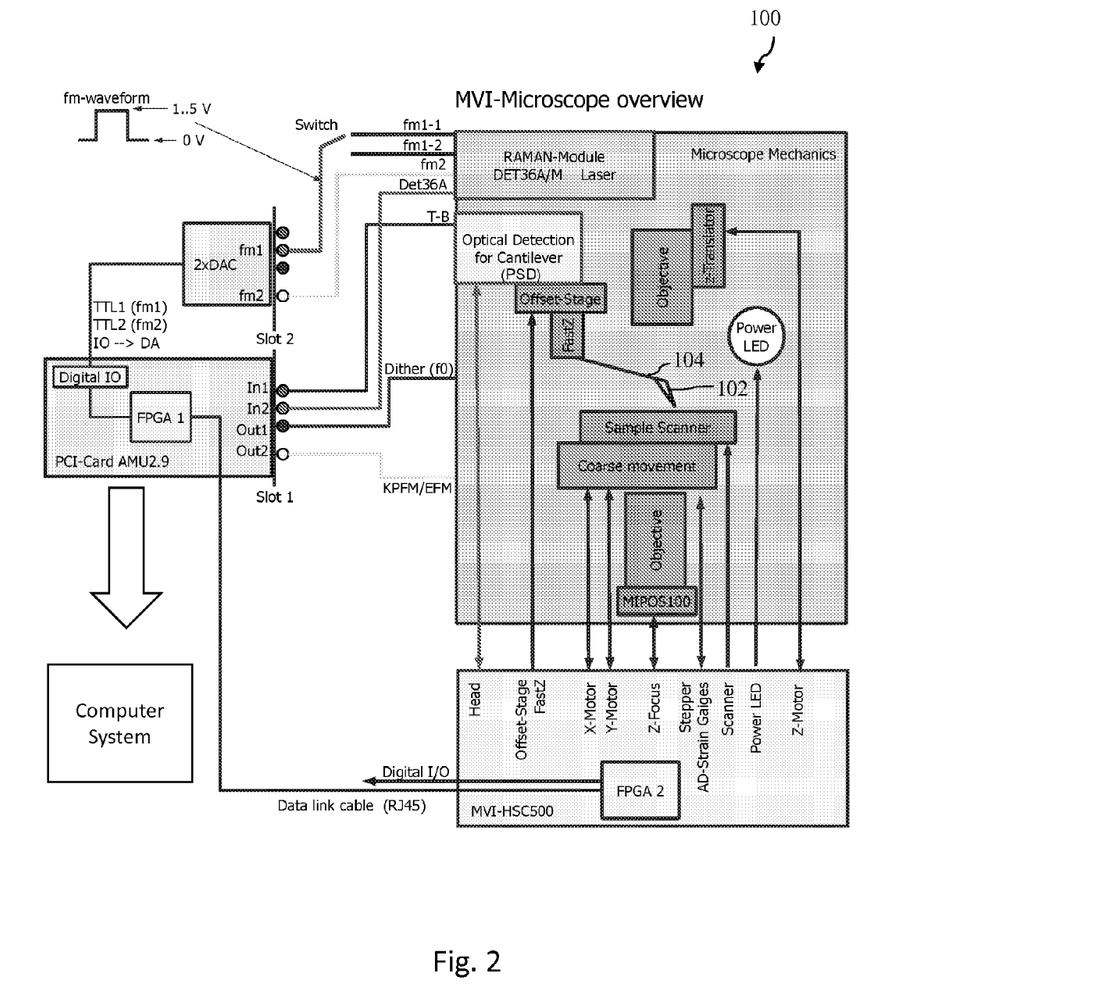
FIG. 2 is a schematic of the Raman force microscope in accordance with an embodiment of the invention.

With reference to FIGS. 1 and 2, a Raman force microscope in accordance with an embodiment of the invention is shown. The Ramon force microscope is an AFM-based microscope that utilizes Raman effect to achieve enhanced spatial resolution as compared to other comparable approaches, including tip-enhanced Raman spectroscopy (TERS).

The Raman effect is the inelastic scattering of a photon. When photons are scattered from an atom or molecule, most photon are elastically scattered with unchanged energy and wavelength. However, a small portion of the scattered photons is scattered with changed energy and wavelength, which is the result of the Raman effect. Due to the scattering of photons produced by the Raman effect, conventional Raman-based microscopes detect the Raman effect by irradiating a sample with an intense light source and detecting the minute amount of frequency shifted, scattered light. However, the Raman force microscope 100 detects the Raman effect in a completely new and unexpected manner by mechanically detecting Raman molecular vibrational resonances, rather than detecting Raman-induced scattered photons. As described in more detail below, the Raman force microscope creates a force interaction through optical parametric down conversion between excited, vibrating molecules, i.e., the object or sample of interest, and a cantilevered nanometer scale probe tip brought very close to the molecules. The mechanical effect of this force interaction on the cantilevered probe tip is then measured to detect the Raman effect on the molecules. Thus, the Raman force microscope uses a completely different mechanism for detecting the Raman effect than conventional Raman-based microscopes that merely detect the inelastically scattered photons due to the Raman effect.

The theory of parametric force detection can be understood by resorting to a simplified classical model. First, it is assumed that a sample being studied, e.g., molecular species, occupies the space between a probe tip on a cantilever and a substrate. If the electric field between the probe tip and the sample is E, then the force F on the probe tip is given by $$F = A\epsilon_0 E^2 [1 + \chi_0 + \partial\chi/\partial q|_{q=0} Q \cos 2\pi v_R t] \qquad (1)$$

where A is some constant, $\epsilon_0$ is free space permittivity, $E^2 = (E_0 \cos 2\pi v_0 t + E_1 \cos 2\pi v_1 t + E_2 \cos 2\pi v_2 t)^2$, $E_0$, $E_1$, $E_2$ being the electric field amplitudes of the beams at $v_0$, $v_1$, $v_2$ respectively, $\chi_0$ is the linear susceptibility of the sample, $\partial\chi/\partial q|_{q=0} Q \cos 2\pi v_R t$ is the non-linear susceptibility term, q is the nuclear vibration coordinate, Q is the nuclear vibration amplitude and $v_R$ is the Raman resonance frequency.

Since the cantilever cannot respond at optical frequencies, the following time averaged force <F> is calculated from equation (1):

$$<F> = A\epsilon_0(1+\chi_0)[E_0^2/2 + E_1^2/2 + E_2^2/2] + A\epsilon_0(\partial\chi/\partial q|_{q=0} Q [E_1 E_2 < \cos 2\pi(v_1-v_2)t \cos 2\pi v_R t>] \qquad (2)$$

The first term in equation (2) is simply the force resulting from the average power incident on the probe tip, while the second term is the force resulting from the Raman oscillations parametrically down converted to a detectable mechanical frequency. If $E_0$ and $E_1$ are modulated in antiphase at $f_m$ and balanced to create a constant power at the probe tip, then the first term in equation (2) is constant. At Raman resonance, when $(v_1-v_2)=v_R$, where $v_1$ is the frequency of the pump laser light, $v_2$ is the frequency of the stimulating laser light and $v_R$ is the Raman resonance frequency, which is the condition for stimulated excitation, a force from the second term is created, which is given by $<F>_{Raman} = (A\epsilon_0/2) \partial\chi/\partial q|_{q=0} Q[E_1 E_2]$.

This term is modulated on and off at $f_m$, which can be detected as Raman signal. An alternative technique to detect a background free Raman signal would be to modulate $E_1$ at $f_1$ and $E_2$ at $f_2$ such that either $f_m = f_1 - f_2$ or $f_m = f_1 + f_2$. In this case, the balancing optical beam at $v_0$ can be eliminated.

In order to create and detect Ramon force, the Raman force microscope 100 uses components commonly found in an atomic force microscope. In the illustrated embodiment, the Raman force microscope uses a tapping mode AFM technique. However, in other embodiments, the Raman force microscope may uses other scanning probe microscopy techniques. As shown in FIGS. 1 and 2, the Raman force microscope includes a probe tip 102 on a cantilever 104, which is connected to a dither piezoelectric component ("Dither Piezo" in FIG. 1). The dither piezoelectric component is used to drive the cantilever at near a resonance frequency of the cantilever $f_0$ so that the cantilever oscillates at the resonance frequency over a sample, which is positioned on a PZT flexure XYZ sample scanner. As used herein, near a resonance frequency means within the range of frequencies defined by the full width at half maximum of the resonance curve. The sample scanner includes a mechanism to move the sample with respect to the probe tip. In the illustrated embodiment, the scanner mechanism is configured to move the sample scanner in coarse X, Y and Z directions. As used herein, the X and Y directions are perpendicular directions that are parallel to the upper surface of the sample scanner, and the Z direction is the direction normal to the upper surface of the sample scanner. In addition, the cantilever is connected to a fast Z piezoelectric component ("Fast Z" in FIG. 1) that can move the cantilever in the Z direction and an offset stage mechanism that can move the cantilever in the X and Y directions. However, in other embodiments, the Raman force microscope may be designed so that only one of the cantilever and the sample scanner can be moved, or so that the cantilever and the sample scanner may be limited in their movements to one or more directions.

The Raman force microscope 100 also includes a laser and a position sensitive detector (PSD). The laser and the PSD are positioned to emit light onto the cantilever 104 and receive the light reflected off the cantilever at the PSD. In FIG. 1, a reflective element is shown that is positioned to reflect the light from the laser onto the cantilever. In other embodiments, the Raman force microscope may eliminate the reflective element by positioning the laser so that the light from the laser reaches the cantilever without the reflective element. In addition, although not illustrated, the Raman force microscope may include one or more optical elements to focus or manipulate the light from the laser to the cantilever or from the cantilever to the PSD. Furthermore, in other embodiments, the laser may be any type of an electromagnetic source that emits electromagnetic radiation, and the PSD can be any type of a PSD that can detect that electromagnetic radiation to sense positional changes of the cantilever, e.g., oscillation of the cantilever. In other embodiments, the laser and the PSD may be absent, and the deflection of the cantilever may be measured via voltage signal generated from strain sensor that is part of the cantilever structure.

In order to create a Raman force interaction between the probe tip 102 and the sample, the Raman force microscope 100 includes at least two lasers to focus two collinear optical beams, a pump beam at frequency $v_1$ and a stimulating beam at frequency $v_2$, on the probe tip and a diffraction limited spot on the sample to efficiently stimulate molecular vibrations at frequency $(v_1-v_2)$. In principle, the Raman force microscope only requires one fixed laser at frequency $v_1$ and one tunable laser that can emit over a certain frequency range $v_{2min}$ to $v_{2max}$, where $v_2$ is within this range. Thus, in FIG. 1, the Raman force microscope is shown to include a fixed wavelength laser that emits light at frequency $v_1$ and a variable wavelength that can emit light over the frequency range $v_{2min}$ to $v_{2max}$ (note: wavelength is inversely related to frequency). However, if the tunable laser does not sufficiently cover the entire desired frequency range, two or more fixed lasers may be used to cover the entire frequency range or increase the frequency range. In the implementation illustrated in FIG. 2, the Raman force microscope includes a tunable laser that covers from 770 nm to 850 nm and two fixed lasers at 702 nm and 764 nm, which are included in a Raman-Module. Regardless of the number of fixed lasers included in the Raman force microscope, only one of the fixed lasers will be operating as the pump laser, and the tunable laser will be operating as the stimulating laser. In other embodiments, the fixed and tunable lasers can be any type of electromagnetic sources that emit electromagnetic radiations.

The Raman force microscope 100 further includes a signal generator, which is labeled "2×DAC" in FIGS. 1 and 2. The signal generator is configured to generate square or sinusoidal wave modulation signals, fm1 and fm2, with variable on-voltage (e.g., the on-voltage may range from 1 V to 5 V). The magnitude of the on-voltage of fm1 and fm2 determines the output power of a fixed wavelength laser and the tunable wavelength laser, respectively. In the implementation illustrated in FIG. 2, one of the two fixed lasers, fm1-1 or fm1-2, is chosen by a switch. In implementations with more fixed wavelength lasers, e.g., four wavelength lasers, the switch would be configured to select one from fm1-1, fm1-2, fm1-3, or fm1-4.

The light from the fixed and the tunable lasers are coupled into a polarization maintaining single mode optical fiber. A small fraction of the combined beam is directed to a fast photo-diode power detector, which is labeled "Det36A" in FIGS. 1 and 2, in order to measure the power of each laser light. The output of the Det36A is fed into a dual frequency lock-in amplifier (using input In2 on PCI-Card AMU2.9 in FIG. 2), which can measure the power density of the two laser lights independently by "locking" onto the respective modulation frequencies. The measured power intensity is used to either increase or decrease the magnitude of the on-voltage for fm1 and fm2 so that the measured power intensity is maintained constant as the operating frequency of the tunable laser is changed.

The combined laser light from the fiber is focused onto the plane of the apex of the probe tip 102 with an objective lens, which is mounted on a manual coarse Z-translation stage and a fine PZT controlled Z-focus stage (labeled "MIPOS100" in FIGS. 1 and 2). The inverted objective lens is also used to see the probe tip and the sample from underneath via a CCD camera (shown in FIG. 1). In order to provide light for the CCD camera, the Raman force microscope 100 includes a light source ("power LED" in FIGS. 1 and 2) that uses an objective lens, which is controlled by a z-translator.

The sample to be examined by the Raman force microscope 100 is mounted on to a sample holder, which is mounted onto the PZT flexure XYZ sample scanner. The XYZ sample scanner is mounted on the XY coarse movement stage so as to access different regions of the sample. In order to generate a strong Raman force signal, the probe tip 102 needs to stay close (on the order of one nanometer) to the sample surface while the pump and stimulating lasers are focused onto the apex of the probe tip. In order to keep the probe tip close to the sample surface while the sample is being scanned, the technique utilized in atomic force microscope (AFM) is used. In AFM, a micro-fabricated cantilever with an integrated tip is used as a force sensor. A cantilever has well-defined resonance frequencies f0 and f1, the frequencies f0 and f1 being the first and second modes of vibration, respectively. For a rectangular shaped cantilever, the frequency f1 is rough six times the value of f0. To measure the force that exists between the apex of the probe tip 102 and the sample surface, the cantilever 104 is driven (via Dither (f0) in FIG. 1) to vibrate near its first resonance frequency with oscillation amplitude that ranges from a few nanometer to about 100 nanometer while the probe tip is far away from the sample surface. The vibration of the cantilever is measured by shining a laser light from the laser onto the back of the cantilever and monitoring the reflected laser light via the PSD. The output (labeled T-B in FIG. 1) from the PSD is monitored by a lock-in amplifier (via In1 input to the PCI-Card AMU2.9 in FIG. 1) which is locked onto the same frequency as the driving frequency. As the vibrating cantilever is moved closer (to a distance of a few nanometers) to the sample surface, the oscillation amplitude will become reduced due to the Van der Waals force between the tip and the sample. An operational set point can be established by setting the desired amplitude reduction. As the sample is scanned with respect to the probe tip, the amount of the amplitude reduction will change according to the changing distance between the probe tip and the sample surface (the closer the tip is to the surface, greater the amplitude reduction) due to the changing surface topography of the sample. The value of the amplitude reduction at different (X, Y) position will reflect the sample topography.

A more efficient way to map the surface topography is to record the amount of adjustment in the Z direction that the sample scanner needs to make to keep a constant tip-sample distance so as to maintain a constant amplitude reduction as the sample is scanned. In the illustrated implementation, the Raman force microscope 100 uses two Z-translation mechanisms: one slower-speed Z direction mechanism that is part of the sample scanner has a large range (e.g., ~20 microns) to compensate for large sample topography and the faster-speed Z direction mechanism (labeled "FastZ" in FIG. 1) that moves just the probe tip has a short range (e.g., ~1 micron) to compensate for small sample topography. This division of z-scanner movement allows the Raman force microscope to scan samples at higher speed when changes in the sample topography are not significant. The Raman force microscope therefore measures the sample topography while maintaining a fixed nanometer scale distance between the probe tip and the sample surface, which allows good Raman force signals to be obtained. Various components of the Raman force microscope are controlled by a controller ("VMI-HSC500" in FIG. 2) in conjunction with a computer system in which the PCI-Card AMU2.9 is installed.

The Raman force between the apex of the probe tip 102 and the sample surface will be present when there is stimulated Raman scattering by satisfying the condition, when $(v_1-v_2)=v_R$, where $v_1$ is the frequency of the pump laser light, $v_2$ is the frequency of the stimulating laser light and $v_R$ is the Raman resonance frequency. This force will be modulated at the driving frequency f0 of the cantilever and will be added to the force arising from the sample topography. However, there would be virtually no way to differentiate the two contributions to the measured force by measuring the PSD output at the driving frequency. In order to measure the Raman force independently, the Raman force microscope 100 utilizes the fact that the Raman force between the probe tip and the sample is non-linear, and thus, "mixes" different inputs. Therefore, if the pump laser and the stimulating laser are modulated at the frequencies fm1 and fm2, respectively, so that the two laser beams are focused onto the apex of the probe tip, the laser beams will mix to create beams at fm1+fm2 and fm1-fm2. Since the probe tip is vibrating at near the frequency f0, the mixing of the two beams with f0 will produce Raman force at the following frequencies: f0+fm1+fm2, f0-fm1-fm2, f0-fm1-fm2, and f0-fm1+fm2. Note that the Raman force is no longer at the driving frequency f0. While it is in principle possible to set either the frequency fm1 or fm2 equal to zero in order to simplify the operation, such a setup introduces a contribution of image force (image force is described in U.S. Provisional Patent Application Ser. No. 61/401,495, filed on Aug. 10, 2010, which is incorporated herein by reference) that will make the interpretation of the Raman force more difficult. The force interactions at the four mixed frequencies will be present in the T-B PSD output. However, since the frequencies are away from the resonant frequency f0, the vibration amplitude at those frequencies will be extremely small, usually beyond the detection level. However, if the value of any one of the four mixed frequencies happens to lie on top of the second resonance mode f1 of the cantilever, the vibration amplitude caused by the Raman force will be greatly amplified. In the operation of the Raman force microscope, the value of the frequencies fm1 and fm2 are chosen such that the frequency of one of the four mixed signals actually coincide with the frequency f1. The dual frequency lock-in amplifier then is operated at both near the driving frequency f0 for feedback controlling the tip-sample distance and the second resonance frequency f1 for detecting the Raman force signal. In other embodiments, the cantilever may be driven at any resonance mode of the cantilever and one of the mixed signals may be detected at any other resonance mode of the cantilever, as described above.

The Raman force signal at the second resonance frequency f1 of the cantilever 104 is processed in the computer system in which the PCI-Card AMU2.9 is installed. The computer system includes many components commonly found in a personal computer, such as one or more processors, memory, a display and input devices, e.g., keyboard and mouse. The Raman force signal is used to produce an image of the sample that shows varying Raman force at different locations of the sample. The signal at the first resonance frequency f0 of the cantilever is also processed in the computer system to produce a topographical image.

In a particular implementation, the Raman force microscope uses a cantilever with stiffness constant k=3 N/m and first mechanical resonance $f_0$=65 KHz. The cantilever includes a gold coated, scanning probe microscope tip (nominal radius of 10 nm). In addition to a pump laser and a stimulating laser, in order to eliminate any spurious effects on the force detection due to pump beam modulation, another laser is modulated to produce a third collinear pump beam (optical frequency $v_0$) also at frequency $f_m$ but 180° out of phase with the first pump beam modulation. The optical power of this third beam is adjusted so that the total modulated component of power presented at the sample surface is zero. Additionally, the optical frequency $v_0$ is chosen such that $(v_0-v_2)$ lies outside any Raman resonances of the sample. In this way, any force modulation detected at the frequency $f_m$ is ensured to be purely due to the stimulated Raman effect. The need for the third beam at frequency $v_0$ is obviated by modulating the two beams at $v_1$ and $v_2$ with modulation frequencies $f_1$ and $f_2$ respectively such that $f_m=f_1+f_2$ or $f_m=f_1-f_2$.

The three collinear laser beams that are used in this implementation are $\lambda_0$ ($v_0$)=633 nm, $\lambda_1$ ($v_1$)=594.1 nm, and $\lambda_2$ ($v_2$)=656 nm. These laser beams are used to illuminate a 10 nm gold coated silicon tip by using an oil immersion objective lens (NA=1.45) focusing via a glass microscope cover slide. The focused laser beams excite a Raman resonance of the object on the glass slide. Depending on whether a laser, an electromagnetic or another energy source is used, the cantilever probe tip can be coated with other appropriate metals as would be known to those of skill in the art. Such metals include, but not limited to, coinage metals such as Platinum, Gold, Silver, and Copper as well as ferromagnetic metals such as Nickel. In another embodiment, the tip of the cantilever is not coated. As the tip approaches a sample, the excited molecules generate an attractive force and force gradient on the probe tip, both modulated at the pump modulation frequency $f_m$. To further enhance the force interaction, a radial polarizer (ARCoptix) is used at the entrance pupil of the objective to ensure that the optical electric field oscillation lies along the axis of the probe tip. The optical power of each beam at the entrance pupil of the objective is nominally adjusted to be approximately 200 μW.

In another embodiment, where a broad range of Raman shift needs to be measured, both the pump beam at frequency $v_1$ and the stimulating beam at frequency $v_2$ are tunable. In yet another embodiment, an electromagnetic or magnetic excitation device could be used to generate the pump and stimulating signals. In a more general embodiment, one or more energy sources capable of stimulating molecular vibration could be used.

The signal recovery and imaging scheme for this implementation are same as the Raman force microscope illustrated in FIGS. 1 and 2. In this implementation, a laser modulation frequency $f_m$=360 KHz is used. The force gradient signal at the upper sideband $f_0+f_m$=425 KHz is chosen to coincide with the second mechanical resonance of the cantilever and can be detected using a lock-in amplifier. The reference for the lock-in can be derived by mixing the $f_0$ and $f_m$ drive signals in a double balanced mixer followed by a band pass filter centered at $f_0+f_m$.

Figure 3:
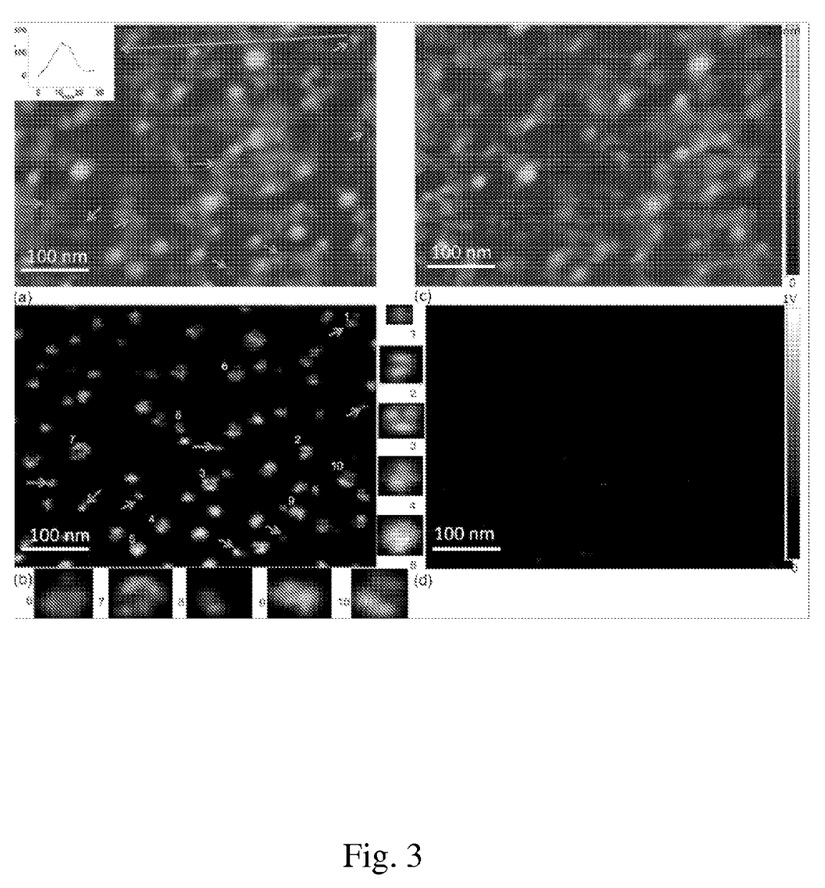
FIG. 3 are topography and Raman images of Coomassie blue dye molecules on glass.

An experiment for this Raman force microscope was performed using Coomassie blue dye. A 30 μL drop of $4 \times 10^{-7}$ mM dye molecules was pipette and dissolved in ethanol onto a clean glass microscope cover slide and allowed to dry. The dye aggregated into molecular clusters with an average dimension of approximately 25 nm while the smallest topography features observed were on the order of 10 nm as shown in FIG. 3(a). The 10 nm feature on the top right corner of FIG. 3(a) is inferred to be a single molecule from the topography scan which shows a height change of less than 500 pm corresponding to the estimated height of a Coomassie blue molecule. In this experiment, the topography and Raman images were simultaneously recorded. FIGS. 3(a) and 3(b) are the topography and Raman images respectively when the laser frequency $v_2$ was temperature tuned so that $(v_1-v_2)$ coincided with the 1625 $cm^{-1}$, vibrational mode of the Coomassie blue molecule. Rich detail is visible in the Raman image as compared with the topography image. FIGS. 3(c) and 3(d) show corresponding images taken with $(v_1-v_2)$ tuned away from this vibrational mode showing no information in the Raman image but essentially the same topography information aside from a small thermal drift.

In FIG. 3(b), the individual molecules within molecular clusters are clearly visible in the Raman image while they are not at all resolved in the topography image of FIG. 3(a). The inset shows clusters of one, two, three and four and five molecules imaged with the Raman force microscope. Some molecules in these clusters appear very bright while others are less bright. These contrast changes are believed to arise from the different orientations of the various molecules within a cluster with respect to the incident electric field of the optical excitation giving rise to different excitation efficiencies. Furthermore, the resolution in the Raman image (5 nm) is superior to that in the topography image (10 nm). This is due to the fact that in the Raman force microscope, both the excitation dipole and the interaction force field are localized to the spatial dimensions of the probe tip since both are near-field interactions. The point spread function of the Raman force microscope is determined by the product of the excitation function and the detector function. This results in a narrower point spread function as compared with other Raman imaging schemes such as Tip Enhanced Raman Spectroscopy where the excitation is in the near-field but the detection is done in the far-field. The S/N of the Raman signal in this experiment was estimated to be 35 dB in 1 Hz bandwidth.

Figure 4:
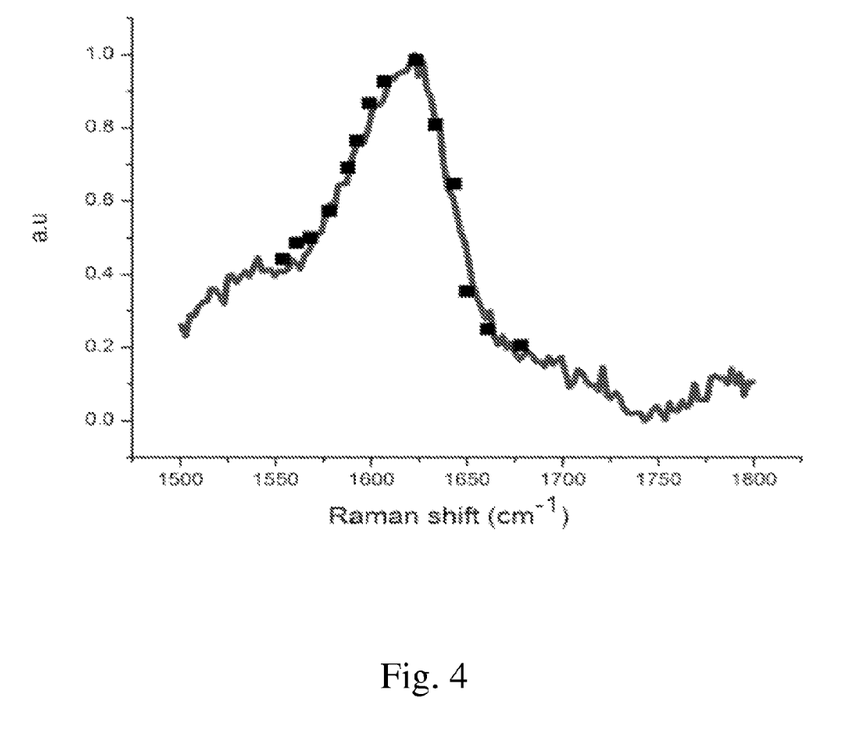
FIG. 4 is a graph of the comparison of recorded Raman spectrum with the probe over a molecular feature in the image shown in FIG. 3(b) obtained by tuning $(v_1-v_2)$ through the 1625 $cm^{-1}$ Raman resonance (solid squares) compared with the Raman spectrum form a thick layer of Coomassie blue molecules and recorded using a commercial Renishaw spectrometer (solid line).

To further validate the imaging concept of the Raman force microscope, the probe over one of the Raman features was located and the response was recorded as a function of $(v_1-v_2)$ by temperature tuning the laser at $v_2$. FIG. 4 shows the recorded Raman spectrum (squares) as compared with a spectrum acquired using a Renishaw spectrometer (solid line); the agreement is excellent. The resolution of the spectrum was 2 $cm^{-1}$, comparable to the resolution of the Renishaw spectrometer.

In another embodiment, time-resolved measurements of the vibrational modes of the photogenerated transient species can be made by using a multi-photon set up. In this set up, pulsed laser beams are used to measure the relaxation dynamics of excited molecules. Typically a pulsed pump laser at frequency $v_1$ coupled with pulsed stimulating laser at frequency $v_2$ will excite the object. This is followed by a set of pulsed probe beams at frequency $(v_1+f_m)$ and at frequency $(v_2+f_n)$ delayed by time t impinging on the object. $(f_m-f_n)$ is chosen such that $(f_0+f_m-f_n)$ coincides with the second resonance of the cantilever to convert the molecular vibrations to a detectable mechanical vibration of the cantilever at $(f_0+f_m-f_n)$. $f_0$ is the first resonance frequency of the cantilever. By choosing the pulse widths and delay $\tau$ appropriately, it should be possible to study processes that occur on time scales as short as $10^{-14}$ seconds.

In another embodiment, $(f_m-f_n)$ is chosen to be within the first cantilever resonance response at $f_0$ and the mechanical vibrations of the cantilever are detected near $f_0$.

In another embodiment, the pulsed probe beams are at frequency $v_1$ and frequency $v_2$ and are amplitude modulated at frequencies $f_m$ and $f_n$ respectively, such that $(f_0+f_m-f_n)$ or $(f_0+f_m+f_n)$ or $(f_0-f_m-f_n)$ or $(f_0-f_m+f_n)$ coincides with the second resonance of the cantilever where the mechanical vibrations of the cantilever are detected.

In another embodiment, the modulation frequencies $f_m$ and $f_n$ are chosen such that $(f_m-f_n)$ lies within the first cantilever response at $f_0$ and the mechanical vibrations of the cantilever are detected near $f_0$.

In another embodiment, the pulsed laser at frequency $v_2$ is replaced by a CW laser at $v_2$ in the schemes described above.

In another embodiment, the time resolved measurement can be used to derive a Raman spectrum spanning a wide wave number range. The detected cantilever vibration signal is mixed with an electronic reference at the cantilever vibration frequency $(f_0+f_m-f_n)$ or $(f_m-f_n)$ using a phase sensitive detector such as a lock-in amplifier. The detected output voltage of the phase sensitive detector is $V_{sig} \cos \theta$, where $\theta$ is the phase difference between the electronic reference and the detected cantilever vibration signal amplitude $V_{sig}$. A graph of the detected output is recorded as a function of the time delay $\tau$. The Fourier transform of this graph yields the Raman frequency response centered at $(v_1-v_2)$ and spanning a frequency range that is on the order of the inverse pulse width of the pulses used in the measurement.

In another embodiment, the probe tip and the object are enclosed in an air-tight chamber such that the chamber can be evacuated to low to high vacuum state or filled with gases and liquids. With the chamber at a moderate vacuum state, it is expected that the sensitivity of the probe to detect the excited molecules to be much greater due to the increased Q of the cantilever. In another embodiment, the probe tip and the sample can be enveloped by liquid in an open liquid container in order to study the samples under liquid.

Yet in another embodiment, the AFM of the Raman force microscope will be operated in a true Non-Contact mode without tapping the object surface while the Raman effect is being detected via the probe. Even though the Raman force microscope is described herein as using an optical detection method for cantilever deflection measurements, a person of skill in the art would appreciate that other method of cantilever deflection methods could be used, such as piezoresistive self-sensing and shear-force techniques.

In conclusion, the Raman force microscopes in accordance with the invention shows that the Raman effect can be detected through an entirely different channel—namely, by measuring the force gradient between a Raman excited molecular feature and a probe tip, e.g., a gold coated probe tip, in a scanning probe microscope. While apertureless near-field microscopes based on light scattering from tips have had great success in imaging nanoscopic objects from the visible to the infrared, including the Raman effect through fluorescence, the signals are very weak because they are based on far-field optical detection of a near-field interaction. It is believed that the detection approach used in the Raman force microscope is readily extended to perform pump-probe experiments on single molecules where it should be possible to use it to measure inter and intra molecular couplings at the single molecular level and track conformational changes within a molecule. Furthermore, the disclosed method may be extended to achieve atomic resolution Raman spectroscopy and imaging. Additionally, the frequencies $v_1$ and $v_2$ can be chosen from IR to UV frequency range depending on the application needs providing great flexibility.

Although a cantilever is used in these examples, tuning forks or other mechanical resonators known to those skilled in the art could be used instead. Moreover, although optical lenses were used to in the above examples to focus the laser beams onto the object/specimen, in embodiments where other energy fields are used, a person of skill in the art would appreciate that other focusing devices could be used, such as electrical beam focusing devices or microwave stripline. Additionally, although the laser beams were shown to be directed to the tip and sample area from the bottom of the sample, the laser beams can be directed to the tip and sample area from the top or from the side of the tip and sample area. For top side illumination, a cantilever with a protruding tip such as AdvancedTEC line of cantilevers from Nano sensors can be used.

Figure 5:
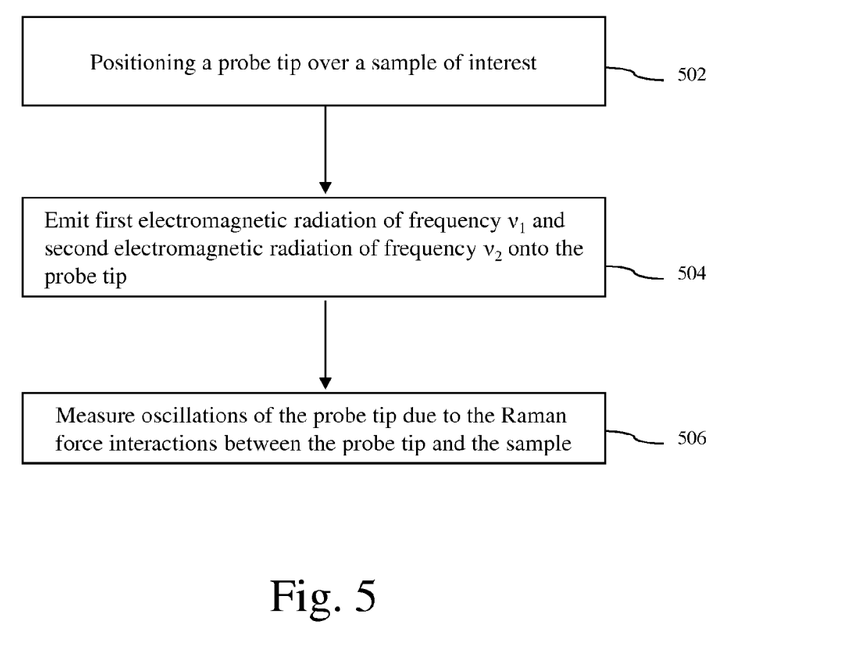
FIG. 5 is a process flow diagram of a method for detecting Raman effect on a sample of interest in accordance with an embodiment of the invention.

A method for detecting Raman effect on a sample of interest in accordance with an embodiment of the invention is described with reference to a flow diagram of FIG. 5. At block 502, a probe tip is positioned over the sample. The probe tip is coupled to a structure that can oscillate the probe tip. Next, at block 504, first electromagnetic radiation of frequency $v_1$ and second electromagnetic radiation of frequency $v_2$ are emitted onto the probe tip. The frequency $v_1$ and the frequency $v_2$ are selected to induce Raman effect on the sample that results in Raman force interactions between the probe tip and the sample. Next, at block 506, oscillations of the probe tip due to the Raman force interactions between the probe tip and the sample are measured.

Although the operations of the method(s) herein are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

It should also be noted that at least some of the operations for the methods may be implemented using software instructions stored on a computer useable storage medium for execution by a computer. As an example, an embodiment of a computer program product includes a computer useable storage medium to store a computer readable program that, when executed on a computer, causes the computer to perform operations, as described herein.

Furthermore, embodiments of at least portions of the invention can take the form of a computer program product accessible from a computer-usable or computer-readable medium providing program code for use by or in connection with a computer or any instruction execution system. For the purposes of this description, a computer-usable or computer readable medium can be any apparatus that can contain, store, communicate, propagate, or transport the program for use by or in connection with the instruction execution system, apparatus, or device.

The computer-useable or computer-readable medium can be an electronic, magnetic, optical, electromagnetic, infrared, or semiconductor system (or apparatus or device), or a propagation medium. Examples of a computer-readable medium include a semiconductor or solid state memory, magnetic tape, a removable computer diskette, a random access memory (RAM), a read-only memory (ROM), a rigid magnetic disk, and an optical disk. Current examples of optical disks include a compact disk with read only memory (CD-ROM), a compact disk with read/write (CD-R/W), and a digital video disk (DVD).

In the above description, specific details of various embodiments are provided. However, some embodiments may be practiced with less than all of these specific details. In other instances, certain methods, procedures, components, structures, and/or functions are described in no more detail than to enable the various embodiments of the invention, for the sake of brevity and clarity.

Although specific embodiments of the invention have been described and illustrated, the invention is not to be limited to the specific forms or arrangements of parts so described and illustrated. The scope of the invention is to be defined by the claims appended hereto and their equivalents.

What is claimed is:

1. An atomic force microscope based apparatus comprising:
    a probe tip for engaging a sample of interest, the probe tip being coupled to a structure that can oscillate the probe tip;
    first and second electromagnetic sources, the first electromagnetic source configured to emit first electromagnetic radiation at frequency $v_1$ onto the probe tip and the second electromagnetic source configured to emit second electromagnetic radiation at frequency $v_2$ onto the probe tip, wherein the frequency $v_1$ and the frequency $v_2$ are selected to induce Raman effect on the sample that results in Raman force interactions between the probe tip and the sample; and
    a sensor configured to measure oscillations of the probe tip due to the Raman force interactions between the probe tip and the sample.

2. The apparatus of claim 1, wherein the frequency $v_1$ and the frequency $v_2$ are selected so that the difference between the frequency $v_1$ and the frequency $v_2$ is equal to a Raman resonance frequency.

3. The apparatus of claim 1, wherein each of the first and second electromagnetic sources is one of a fixed wavelength laser and a tunable laser.

4. The apparatus of claim 1, wherein the first and second electromagnetic sources are modulated at frequencies fm1 and fm2, respectively, to produce Raman force at mixed frequencies f0+fm1+fm2, f0−fm1−fm2, f0−fm1−fm2, and f0−fm1+fm2, where the frequency f0 is a driving frequency of the structure with the probe tip.

5. The apparatus of claim 4, wherein the frequencies fm1 and fm2 are selected so that one of the mixed frequencies f0+fm1+fm2, f0−fm1−fm2, f0−fm1−fm2, and f0−fm1+fm2 is near the second resonance mode frequency f1 of the structure with the probe tip.

6. A method for detecting Raman effect on a sample of interest comprising:
    positioning a probe tip over the sample, the probe tip being coupled to a structure that can oscillate the probe tip;
    emitting first electromagnetic radiation of frequency $v_1$ and second electromagnetic radiation of frequency $v_2$ onto the probe tip, wherein the frequency $v_1$ and the frequency $v_2$ are selected to induce Raman effect on the sample that results in Raman force interactions between the probe tip and the sample; and
    measuring oscillations of the probe tip due to the Raman force interactions between the probe tip and the sample.

7. The method of claim 6, wherein the frequency $v_1$ and the frequency $v_2$ are selected so that the difference between the frequency $v_1$ and the frequency $v_2$ is equal to a Raman resonance frequency.

8. The method of claim 6, wherein the first electromagnetic radiation of frequency $v_1$ and the second electromagnetic radiation of frequency $v_2$ are emitted from at least one of a fixed wavelength laser and a tunable laser.

9. The method of claim 6, wherein the first electromagnetic radiation of frequency $v_1$ and the second electromagnetic radiation of frequency $v_2$ are modulated at frequencies fm1 and fm2, respectively, to produce Raman force at mixed frequencies f0+fm1+fm2, f0−fm1−fm2, f0−fm1−fm2, and f0−fm1+fm2, where the frequency f0 is a driving frequency of the structure with the probe tip.

10. The method of claim 9, wherein the frequencies fm1 and fm2 are selected so that one of the mixed frequencies f0+fm1+fm2, f0−fm1−fm2, f0−fm1−fm2, and f0−fm1+fm2 is near the second resonance mode frequency f1 of the structure with the probe tip.

\* \* \* \* \*